US011154092B2

(12) United States Patent
Kessler et al.

(10) Patent No.: US 11,154,092 B2
(45) Date of Patent: Oct. 26, 2021

(54) EVAPORATOR DEVICE, CONSUMABLE UNIT, INHALER AND METHOD FOR MANUFACTURING ELECTRICALLY HEATABLE HEATING BODIES AND SEAL CARRIERS

(71) Applicant: HAUNI MASCHINENBAU GMBH, Hamburg (DE)

(72) Inventors: Marc Kessler, Hamburg (DE); Markus Schmidt, Geesthacht (DE)

(73) Assignee: HAUNI MASCHINENBAU GMBH, Hamburg (DE)

( * ) Notice: Subject to any disclaimer, the term of this patent is extended or adjusted under 35 U.S.C. 154(b) by 64 days.

(21) Appl. No.: 16/696,268

(22) Filed: Nov. 26, 2019

(65) Prior Publication Data

US 2020/0163383 A1 May 28, 2020

(30) Foreign Application Priority Data

Nov. 28, 2018 (DE) .......................... 102018130106.5

(51) Int. Cl.
*A24F 40/46* (2020.01)
*F16J 15/34* (2006.01)

(52) U.S. Cl.
CPC .............. *A24F 40/46* (2020.01); *F16J 15/34* (2013.01)

(58) Field of Classification Search
CPC ....................................................... A24F 40/46
See application file for complete search history.

(56) References Cited

U.S. PATENT DOCUMENTS

| 10,925,313 | B1* | 2/2021 | Han ........................ A24F 40/10 |
| 2006/0196968 | A1 | 9/2006 | Rabin et al. |
| 2016/0345630 | A1 | 12/2016 | Mironov et al. |
| 2017/0095624 | A1* | 4/2017 | Davidson ............... H05B 3/265 |
| 2017/0106113 | A1 | 4/2017 | Meinhart et al. |
| 2019/0053539 | A1* | 2/2019 | Davis ...................... A24F 40/46 |
| 2019/0246696 | A1 | 8/2019 | Schmidt et al. |
| 2020/0163383 | A1* | 5/2020 | Kessler ............... A61M 11/042 |

FOREIGN PATENT DOCUMENTS

| CN | 204499489 U | 7/2015 |
| DE | 10 2017 111 119 A1 | 5/2017 |
| DE | 10 2016 120803 A1 | 5/2018 |
| WO | WO 2017/220274 A1 | 12/2017 |

OTHER PUBLICATIONS

Examination Report issued by the European Patent Office dated Jul. 28, 2020 for parallel European Patent Application No. 19 211 181.3.
1st Examination Report issued by the German Patent and Trademark Office dated Aug. 9, 2019 with respect to priority German Patent Application No. 10 2018 130 106.5.

* cited by examiner

*Primary Examiner* — James Harvey
(74) *Attorney, Agent, or Firm* — Saliwanchik, Lloyd & Eisenschenk (57) ABSTRACT

An evaporator device for an inhaler, in particular for an electronic cigarette product comprises an electrically heatable heating body having at least one passage opening for evaporating liquid contained in the passage opening and a carrier for retaining the heating body. The evaporator device has a sealing device, and the sealing device is arranged between the heating body and the carrier and encloses the at least one passage opening in a sealing manner.

15 Claims, 7 Drawing Sheets

EVAPORATOR DEVICE, CONSUMABLE UNIT, INHALER AND METHOD FOR MANUFACTURING ELECTRICALLY HEATABLE HEATING BODIES AND SEAL CARRIERS

CROSS REFERENCE TO RELATED APPLICATIONS

This application claims priority under 35 U.S.C. § 119(e) of German Patent Application No. DE 102018130106.5, filed on Nov. 28, 2018, which is incorporated herein by reference in its entirety.

FIELD OF THE INVENTION 1.0 The present invention relates to an evaporator device for an inhaler, in particular for an electronic cigarette product, comprising an electrically heatable heating body having at least one passage opening for evaporating liquid contained in the passage opening and a carrier for retaining the heating body. The invention also relates to a consumable unit, an inhaler and a method for manufacturing a plurality of electrically heatable heating bodies and for manufacturing a plurality of seal carriers, each for an evaporator device.

BACKGROUND OF THE INVENTION

Conventional inhalers are based on wick coil technology. Capillary forces transport the liquid from a liquid store along a wick until the liquid is heated by an electrically heatable coil and therefore evaporates. However, wick coil technology has the disadvantage that a lack of liquid supply can lead to local overheating, which can release harmful substances. That is the so called "Dry Puff" and it is important to avoid it.

In an evaporator device known in the prior art, the liquid is transported from a liquid store to the passage opening, where the liquid is heated and evaporated. Unlike wick coil technology, other liquid transport technologies can lead to leakage.

The heating body is retained by the carrier and therefore the heating body and the carrier are mechanically interconnected. As a result, the heat from the heating body is dissipated into the carrier. The heat dissipated into the carrier may adversely affect the mechanical properties of the carrier and/or affect the user experience. In addition, the heat dissipation or heat transport from the heating body into the carrier represents an unnecessary energy load for an electrical energy store of the inhaler.

BRIEF SUMMARY OF THE INVENTION

It is the object of the invention to provide an improved evaporator device to avoid leakage and advantageously untargeted heat transport.

The object is solved by the features of the independent claims.

The invention revealed that a side of the heating body facing the carrier typically has a different surface finish than a side of a component part other than the one facing the heating body contacting the heating member. Due to the different surface finishes, unevenness occurs through which liquid can penetrate, leading to leakage. In order to compensate for unevenness between the side of the heating body facing the carrier and the surface of the component part facing the heating body, said component part being different from the heating body, and in order to prevent leakage, the evaporator device according to the invention has a sealing device arranged between the heating body and the carrier. The sealing device therefore serves to improve the fluid sealing of the heating body against the carrier.

The sealing device is arranged in such a manner that the sealing device encloses the at least one passage opening in a sealing manner, in particular in a liquid-sealing manner. The sealing device according to the invention and its arrangement allow the liquid to move freely only between the heating body and the carrier and in the region of the at least one passage opening. This prevents liquid from leaking out. In particular, a leakage is prevented at a possible unevenness between the heating body and the carrier.

The invention also revealed that the thermal coupling between the heating body and the carrier can be reduced by means of a sealing device arranged between the heating body and the carrier when there is a direct and surface contact between the heating body and the carrier. Since the sealing device is located between the heating body and the carrier, the heat transport between the carrier and the heating body is inhibited and the dissipation of the heat from the heating body to the carrier is reduced.

The sealing device advantageously encloses the at least one passage opening completely in order to improve the sealing of the at least one passage opening. The heating body may comprise a plurality of passage openings, wherein the sealing device may completely enclose one, a plurality or all of the passage openings. The sealing device advantageously encloses all passage openings in order to provide an effective embodiment.

Preferably, a surface contacting the sealing device has a recess corresponding to the geometry of the sealing device for inserting the sealing device in order to guide the sealing device during assembly or as a joining aid, to enable a flatter construction and/or to be able to provide a higher liquid sealing. In particular, the carrier may have a recess for inserting the sealing device corresponding to the geometry of the sealing device, in particular the sealing member.

The sealing device, in particular the sealing member, and the heating body are advantageously interconnected in a material-tight manner in order to improve the liquid sealing or to ensure that no liquid can escape between the sealing device and the heating body. The combination of the heating body and the sealing device or sealing member can simplify the assembly of the evaporator device and reduce the number of component parts to be assembled during manufacturing compared to an embodiment in which the sealing member is a separate component part, i.e. a component part which is not connected to the heating body in a material-tight manner.

In a preferred embodiment, the sealing device comprises one or a plurality of sealing members to provide an effective embodiment of the invention. In a preferred embodiment, the sealing device comprises a plurality of sealing members, arranged, for example, radially spaced around the passage opening, to improve the tightness completely and/or, for example, in particularly exposed regions. Each sealing member preferably encloses the passage opening in a liquid-sealing manner, in particular completely and/or at least partially. The further sealing member(s) can be connected to the heating body or to a surface contacting the heating body in a material-tight manner.

The sealing device, in particular the sealing member, is preferably softer than the heating body and/or the carrier in order to be able to compensate for unevenness, in particular by a deformation of the sealing device in a frictional connection between the heating body and the carrier, and therefore to improve the sealing. In particular, "soft" means that the sealing device has, at least in the assembled state, a lower modulus of elasticity than the heating body and/or the carrier. In a method step preceding the assembled state, for example the assembly and/or manufacture of the evaporator device, the sealing device can also be liquid or semi-liquid, so that the sealing device can be arranged by viscous and/or plastic deformation. The sealing device can be a flexible sealing member to simplify the arrangement and/or the assembly.

Advantageously, the evaporator device comprises a substrate arranged between the carrier and the heating body for thermal decoupling of the heating body and the carrier. The substrate can, for example, consist of a temperature-resistant plastic, such as PEEK, and/or a ceramic material. In particular, the substrate may be plate-like. The thermal decoupling is particularly advantageous if the carrier is made of plastic, for example. The substrate can have a recess corresponding to the geometry of the sealing member for inserting the sealing device as described above.

In a preferred embodiment, the evaporator device has a seal carrier arranged between the carrier and the heating body, wherein the seal carrier comprises at least one seal member in order to improve the liquid sealing. The seal member can be arranged on a surface of the seal carrier contacting the sealing device and/or facing the heating body. In another embodiment, the seal member can additionally or exclusively also be arranged on a surface of the seal carrier facing away from the heating body in order to be able to contact the carrier and/or a substrate and to establish a liquid-sealed contact between the seal carrier and the carrier and/or the substrate.

The sealing device preferably forms a labyrinth seal to improve the liquid sealing. In this embodiment, the sealing device, in particular the sealing member, the seal member and/or preferably further sealing and/or seal members complement each other to form a labyrinth seal. The advantage is that at least the sealing member and, for example, the seal member are arranged on sides and/or surfaces of the heating body and the seal carrier in order to improve the liquid sealing, said sides and/or surfaces being opposite or facing one another.

A consumable unit according to the invention comprises a previously described evaporator device to provide an effective, compact and liquid-sealed component part for an inhaler.

An inhaler according to the invention comprises a previously described evaporator device to provide an effective, compact and liquid-sealed inhaler.

A method for manufacturing a plurality of electrically heatable heating bodies for an evaporator device and having at least one passage opening for evaporating liquid contained in the passage opening comprises providing a plate-like semiconductor material, incorporating a plurality of passage openings extending through the semiconductor material in the direction normal to the surface of the semiconductor material, separating the semiconductor material along at least one separation line to provide the plurality of heating bodies.

The invention revealed that a side of the heating body facing a carrier, which is advantageously metal-free and further advantageously made of silicon, typically has a different surface finish than a side facing the heating body contacting the heating member. According to the invention, the method comprises arranging a number of sealing bodies corresponding to the number of the heating members in such a manner that each passage opening is circumferentially enclosed by a sealing member in order to be able to provide heating bodies for a liquid-sealed evaporator device by the method according to the invention.

It is advantageous to arrange the sealing members before separating the semiconductor material in order to process the semiconductor material before the separating produces a plurality of heating bodies. The order of the heating bodies to be manufactured, which can be arranged exactly on the semiconductor material, can thus be used. Therefore a plurality of heating bodies can be manufactured effectively.

The arranging of the sealing members in a liquid state is preferred in order to be able to apply the sealing members to the heating bodies in a particularly effective manner. The sealing members harden advantageously after the arranging in the liquid state and assume an elastic, flexible or soft state.

The sealing members are advantageously connected in a material-tight manner using the semiconductor material and/or the heating body during the arranging in order to be able to provide a number of component parts as effectively as possible after the arranging of the sealing members.

According to the invention, a method for manufacturing a plurality of seal carriers for sealing electrically heatable heating bodies for an evaporator device and having at least one liquid opening for conducting liquid comprises providing a plate-like material, incorporating a plurality of liquid openings extending through the material in the direction normal to the surface of the material, separating the material along at least one separation line to provide the plurality of seal carriers, and arranging a number of seal members corresponding to at least the number of seal carriers in such a manner that each liquid opening is circumferentially enclosed by a seal member. The invention revealed that the proposed method would be particularly effective by manufacturing seal carriers.

It is advantageous to arrange the seal members before separating the material, which enables a particularly effective arrangement or alignment of the seal members. Further advantageous embodiments can be directly adopted from the manufacturing of electric heating bodies. The material advantageously comprises a thermally insulating, thermally stable and/or chemically inert plastic and/or a ceramic material.

BRIEF DESCRIPTION OF THE FIGURES

The invention will be explained below on the basis of the preferred embodiments with reference to the accompanying drawings. In which.

DETAILED DESCRIPTION

FIGS. 1 to 5 are each an exploded view of an evaporator device 1. The evaporator device 1 comprises an electrically heatable heating body 60 having at least one passage opening 62, as further described with reference to FIG. 13, for evaporating liquid contained in the passage opening 62. In the embodiments according to the invention in FIGS. 1 to 5, the evaporator device 1 comprises a carrier 4 for retaining the heating body 60. The heating body 60 is retained by the carrier 4. For example, the heating body 60 can be retained by the carrier 4 by clamping, plugging, gluing, welding and/or soldering.

Figure 1:
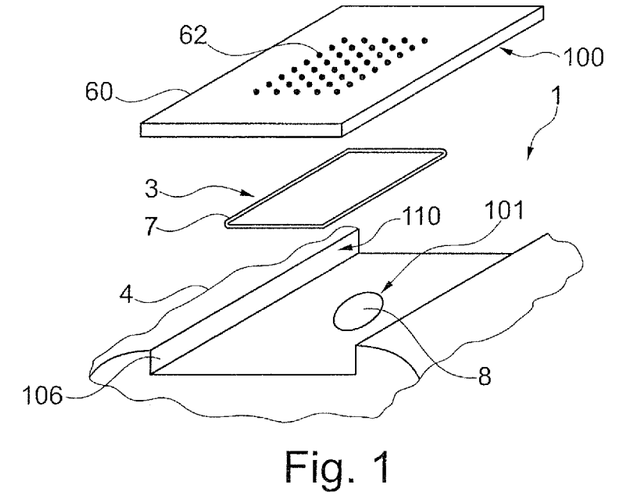
FIGS. 1 to 5 are each an exploded view of an evaporator device according to the invention.

The carrier 4 has advantageously a notch or groove 106. The groove 106 in the example shown in FIG. 1 is dimensioned in order to ensure that the heating body 60 is aligned flush with the flanks 110 defining the groove 106 of the carrier 4 in the assembled state. The arrangement of the heating body 60 inside the groove 106 can, for example, favour the assembly of the evaporator device 1 and improve the liquid sealing.

As shown in FIGS. 1 to 5, the carrier 4 has a conduit opening 8 for conducting liquid. The carrier 4 can be connected to a non-displayed liquid store 18 in a liquid-conducting manner. A liquid store 18 is described with reference to FIGS. 12 and 13.

The liquid store 18 is connected to the heating body 60 via the conduit opening 8 in a liquid-conducting manner. In a preferred embodiment, a wick structure 19 can extend between the liquid store 18 and the heating body 60, for example, inside and/or through the conduit opening 8, which is explained with reference to the schematic illustration in FIG. 12.

The heating body 60 has a plurality of passage openings 62, which, in an advantageous embodiment, can be designated in particular as micro-channels due to their dimensions. In these examples, the passage openings 62 are arranged within a rectangle. However, any other arrangement of the passage openings 62 is conceivable. A detailed description of the heating body 60 is provided in the description with reference to FIG. 13. For manufacturing the heating body 60 please refer to FIGS. 10 and 11 and the corresponding description.

The sealing device 3 encloses the passage opening 62 in a sealing manner, see FIG. 1. The sealing device 3 is arranged between the heating body 60 and the carrier 4.

In the example shown in FIG. 1, the sealing member 7 forms the sealing device 3. The sealing member 7 encloses the passage openings 62 completely. The form of the sealing member 3 in this example is a rounded rectangle, and in other embodiments it can be round, oval, angular or otherwise shaped in order to enclose the passage opening 62.

The sealing member 7 is arranged in such a manner as to contact a side 100 of the heating body 60 facing the carrier 4 and a surface 101 of the carrier 4 facing the heating body. This allows to compensate for a possible unevenness at the contact places between the surface 101 of the carrier 4 and the side 100 of the heating body 60, said unevenness resulting from the surface finish of the heating body 60 and the carrier 4 or the side 100 and the surface 101.

Figure 2:
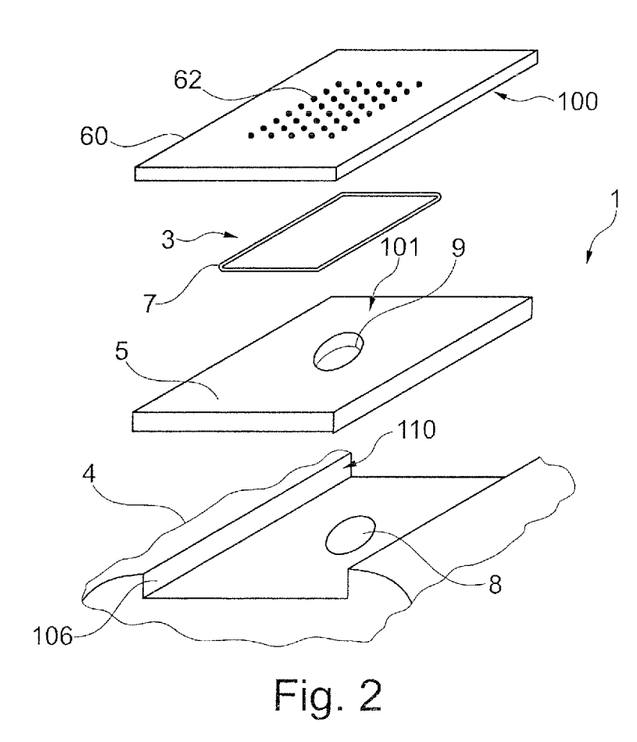

The embodiment according to FIG. 2 is explained with regard to the differences to FIG. 1. In the embodiment shown in FIG. 2, the evaporator device 1 comprises a substrate 5 arranged between the carrier 4 and the heating body 60.

The substrate 5 can be used for thermal decoupling between the heating body 60 and the carrier 4. A substrate 5 is particularly advantageous if the carrier 4 is made of a plastic. In this case, the substrate 5 can be formed advantageously from a thermally stable plastic, such as PEEK, and/or a ceramic material. A ceramic substrate is inert and temperature resistant. By varying the material thickness of the substrate 5, the thermal separation and/or the sealing effect between the carrier 4 and the heating body 60 can be adjusted.

The substrate 5 has a liquid opening 9 for conducting liquid. The liquid opening 9 is advantageously arranged in line with the conduit opening 8 in order to ensure liquid transport. This allows a continuous liquid transport from a liquid store 18 not shown in this drawing through the conduit opening 8 and the liquid opening 9 to the heating body 60.

In this embodiment the sealing member 7 is arranged in such a manner that the sealing member 7 contacts the side 100 of the heating body 60 facing the carrier 4 and a surface 101 of the substrate 5 facing the heating body. This allows to compensate for a possible unevenness at the contact places between the surface 101 of the substrate 5 and the side 100 of the heating body 60, said unevenness resulting from the surface finish of the heating body 60 and the substrate 5.

The groove 106 in the example shown in FIG. 2 is dimensioned in order to ensure that the substrate 5 and/or the heating body 60 are aligned flush with the flanks 110 defining the groove 106 of the carrier 4 in the assembled state.

In FIGS. 1 and 2, the sealing member 7 is shown as a separate component, which may in particular be a standard and temperature resistant O-ring. The sealing member 7 can also be a standard component part in other embodiments. The sealing member 7 can preferably be connected to the heating body 60 in a material-tight manner. It is also possible to provide a sealing member connected to the heating body 60 in a material-tight manner and a separate sealing member as a sealing device 3. The sealing member 7 consists advantageously of a temperature-resistant plastic, for example silicone or rubber.

Figure 3:
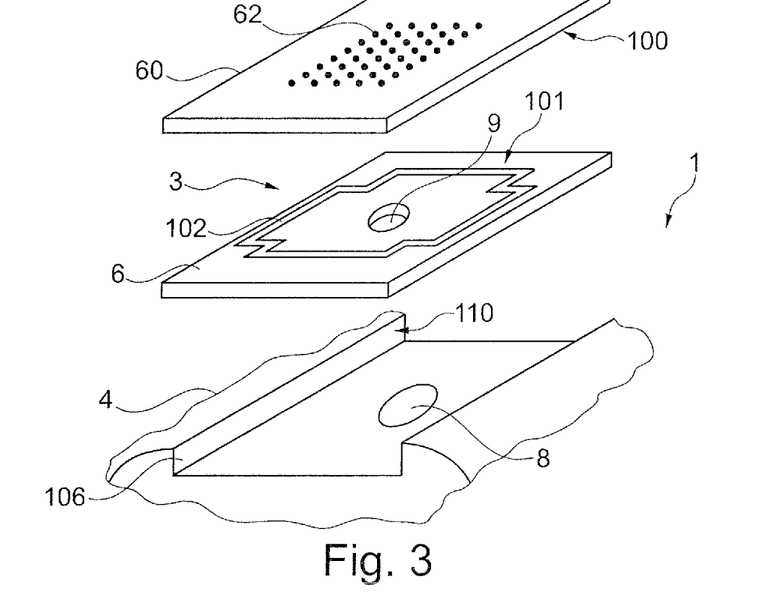
Figure 4:
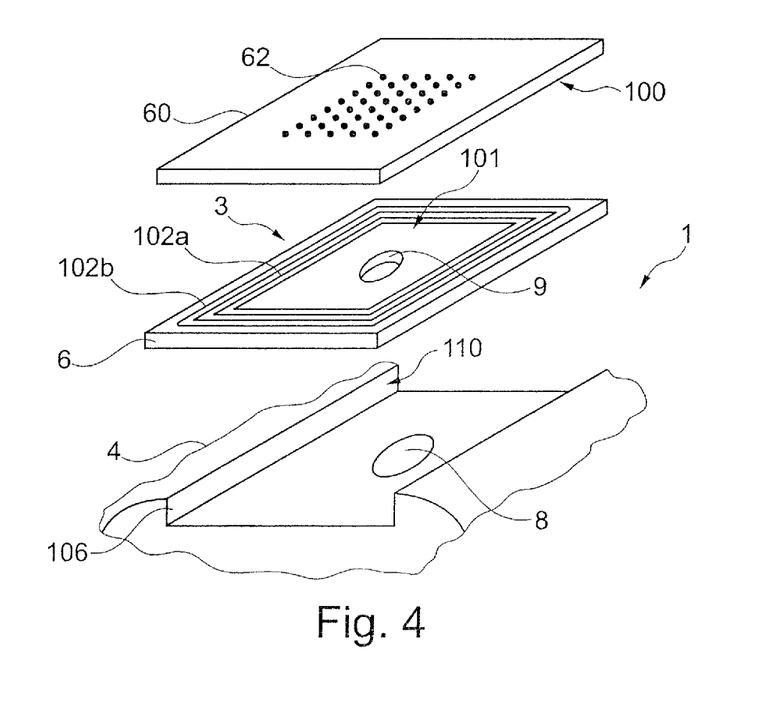

FIGS. 3 and 4 each show an embodiment in which the evaporator device 1 has a seal carrier 6 arranged between the carrier 4 and the heating body 60. The seal carrier 6 comprises in FIG. 3 a seal member 102 and in FIG. 4 a plurality of seal members 102a, 102b. The sealing device 3 in these examples is formed by the seal carrier 6 and/or the seal member(s) 102, 102a, 102b. The seal member 102 in FIG. 3 or the seal members 102a, 102b in FIG. 4 can each be connected to the seal carrier 6 in a material-tight manner. It is also possible that the seal carrier 106 has a recess 105, which is similar to the recess 105 described in FIG. 6, in which the seal member 102 or the seal members 102a, 102b can be inserted and retained. This is an alternative to the material-tight connection between the seal carrier 6 and the seal member 102 or the seal members 102a, 102b.

In this embodiment, the seal member 102 or the seal members 102a, 102b are arranged in such a manner that the seal member 102 or the seal members 102a, 102b contact the side 100 of the heating body 60 facing the carrier 4 and a surface 101 of the seal carrier 6 facing the heating body. This allows to compensate for a possible unevenness at the contact places between the surface 101 of the seal carrier 6 and the side 100 of the heating body 60, said unevenness resulting from the surface finish of the heating body 60 and the seal carrier 6.

The seal carrier 6 shown in FIGS. 3 and 4 has a liquid opening 9 explained with reference to the substrate 5 shown in FIG. 2 for conducting liquid. The seal carrier 6 is advantageously plate-like and can therefore also be designated as a sealing plate. The seal carrier 6 can be dimensioned and formed as the substrate 5 described with reference to FIG. 2. The seal carrier 6 provides an advantageous thermal insulation by, for example, selecting a suitable material and/or geometry, see also FIGS. 8 and 9 and their description.

In FIG. 4 the seal members 102a, 102b are arranged concentrically around the liquid opening 9. Therefore, the seal members 102a, 102b enclose the passage openings 62 completely and in a liquid-sealed manner. The seal members 102a, 102b are radially spaced from one another beginning at the liquid opening 9. In other embodiments, for example, one of the seal members 102a, 102b can only partially enclose the passage openings 62, especially in particularly exposed regions, wherein particularly exposed regions are, for example, the regions where a leakage is most probable.

The groove 106 of the carrier 4 is dimensioned in such a manner that the seal carrier 6 and/or the heating body 60 are aligned flush with the flanks 110 of the carrier 4 defining the groove 106 in the assembled state.

The seal member 102 or the seal members 102a, 102b consist advantageously of a temperature-resistant plastic, for example silicone or rubber.

Additionally to the seal member 102 and/or the seal members 102a, 102b, a sealing member 3 can be provided, as explained with reference to FIGS. 8 and 9.

Figure 5:
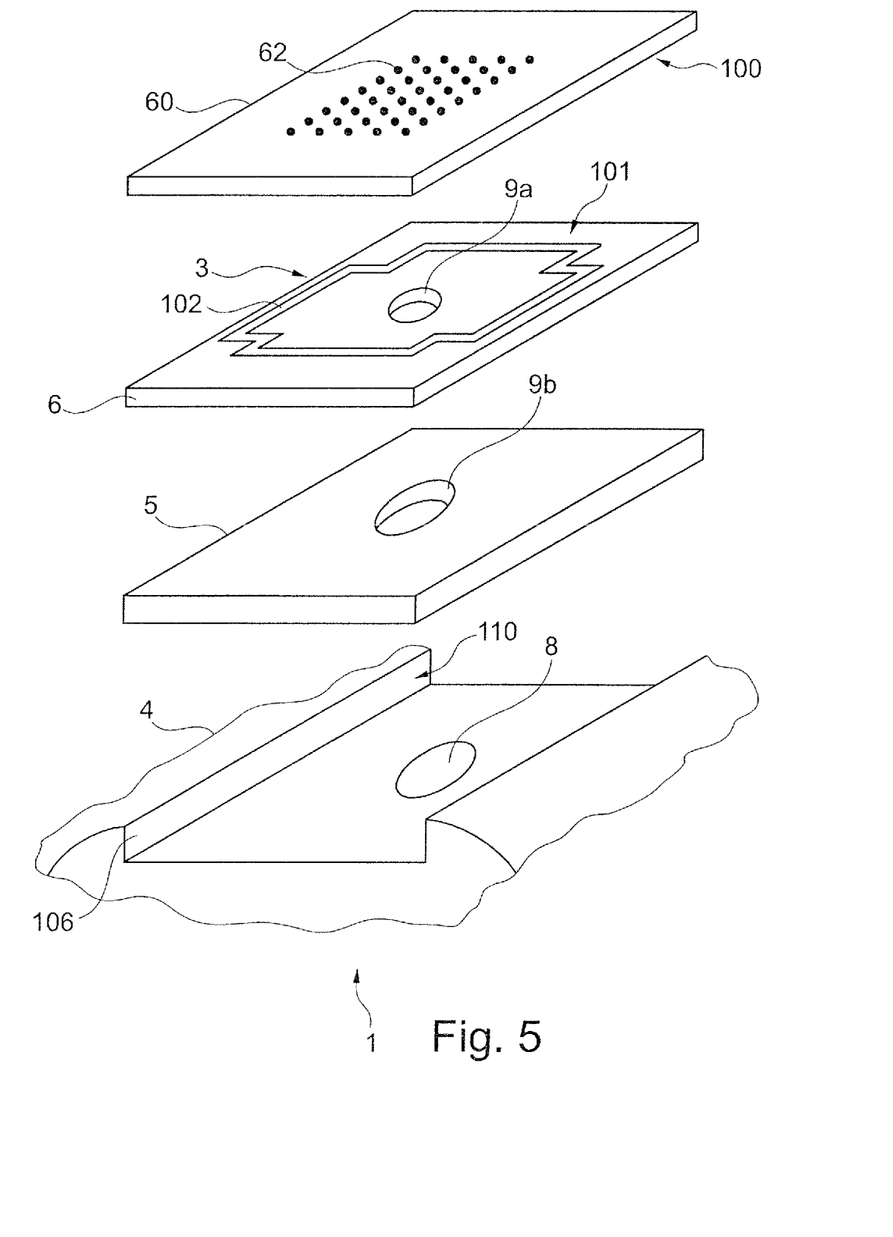

FIG. 5 shows an embodiment in which the evaporator device 1 has a substrate 5 arranged between the carrier 4 and the heating body 60 as explained with reference to FIG. 2 and a seal carrier 6 arranged between the carrier 4 and the heating body 60 as explained with reference to FIGS. 3 and 4. In this case the seal carrier 6 is arranged between the heating body 60 and the substrate 5. The substrate 5 and the seal carrier 6 each have a liquid opening 9a, 9b for conducting liquid, as explained with reference to the substrate 5 shown in FIG. 2.

The groove 106 in the examples shown in FIG. 5 is dimensioned in order to ensure that the substrate 5, the seal carrier 6 and/or the heating body 60 are aligned flush with the flanks 110 defining the groove 106 of the carrier 4 in the assembled state.

The sealing of the component parts, in particular the evaporator device 1, can be improved by the advantageously polished, in particular single-side polished (ssp) surface or side 100 of the heating body 60 and a dimensionally and positionally accurate surface 101 of the substrate 5 and of the carrier 4. One or both sides of the seal member 102, or the seal members 102a, 102b can be applied to the seal carrier 6 and/or one or a plurality of seal members 7 can be applied to the heating body 60.

FIGS. 6 to 9 each show a schematic cross-sectional view of an evaporator device 1.

Figure 6:
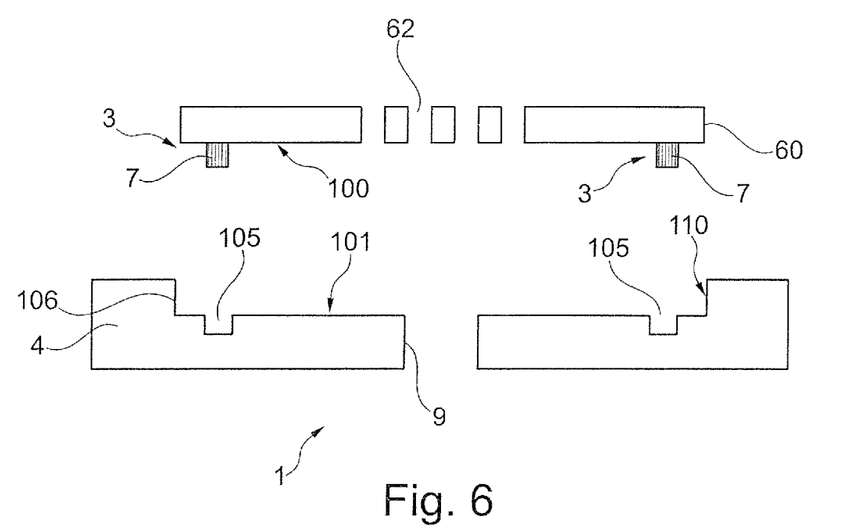
FIGS. 6 to 9 are each a cross-sectional view of an evaporator device according to the invention.

In FIG. 6, the sealing device 3 has a sealing member 7. A surface 101 contacting the sealing member 7 has a recess 105 corresponding to the geometry of the sealing member 7 for inserting the sealing member 7.

The sealing member 7 can have a height equal to the depth of the recess 105. The sealing member 7 has advantageously a width corresponding to the width of the recess 105. Therefore, the sealing member 7 can contact the recess over the entire surface. By inserting the sealing member 7 into the recess 105, this embodiment is particularly liquid-sealed and compact.

The groove 106 is defined by surfaces designated as flanks 110. The flanks 110 can have a height corresponding to the thickness of the heating body 60. The heating body 60 can therefore be inserted flush into the groove 106. As a result, the evaporator device 1 has a flush top surface in the assembled state, which is defined by the heating body 60 and the carrier 4. The depth of the groove 106 can be adjusted to the height of the heating body 60, analogously to the height of the heating body 60 and a substrate 5, of the heating body 60 and a seal carrier 6 and/or of the heating body 60 and a substrate 5 and a seal carrier 6.

Figure 7:
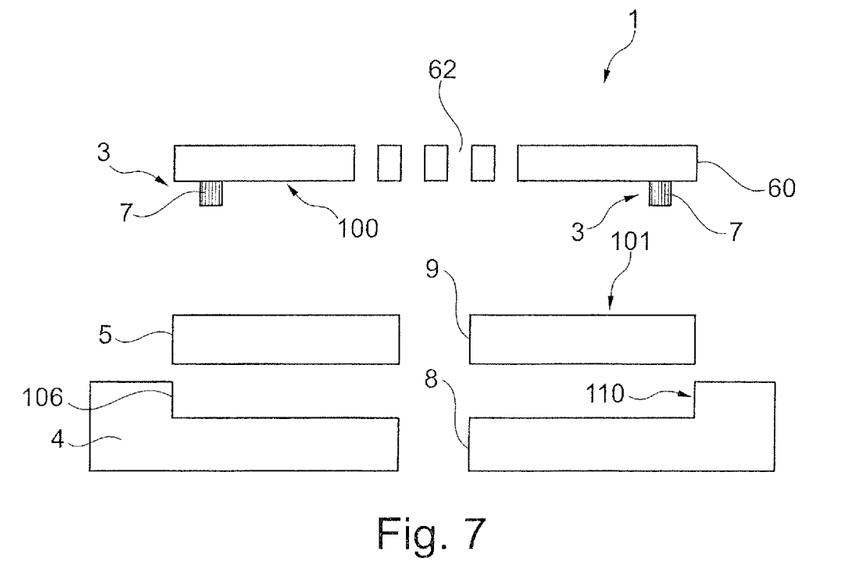

FIG. 7 is a cross section of the embodiment described with reference to FIG. 2 having a substrate 5 arranged between the heating body 60 and the carrier 4. This embodiment is particularly suitable for the thermal decoupling of a heating body 60 and a carrier 4. The substrate 5 and the sealing members 7 each inhibit the heat transport from the heating body 60 to the carrier 4.

Figure 8:
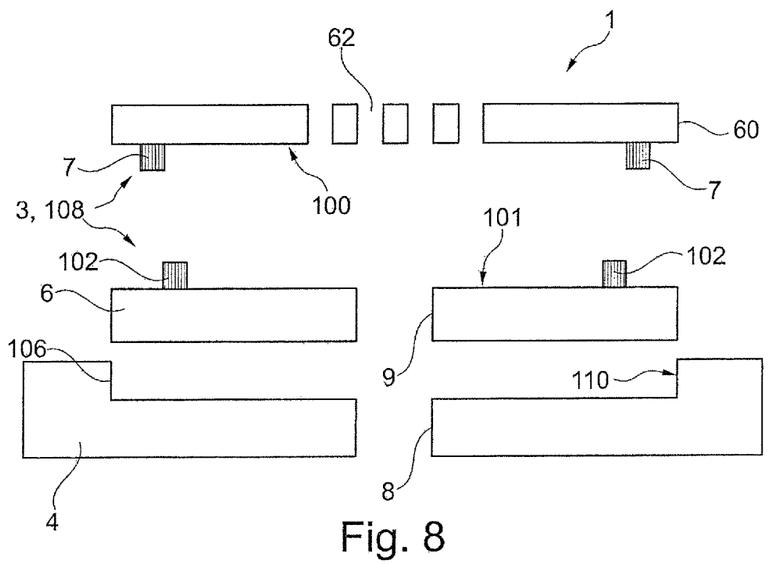

FIG. 8 is a cross section of the embodiment described with reference to FIG. 3 with a seal carrier 6 having a seal member 102 arranged between the heating body 60 and the carrier 4. The sealing device 3 comprises a sealing member 7 and the seal carrier 6 having the seal member 102. The sealing device 3 forms a simple embodiment of a labyrinth seal 108 in the assembled state. This embodiment is particularly liquid-sealed and thermally decouples the heating body 60 and the carrier in a particularly effective manner.

Figure 9:
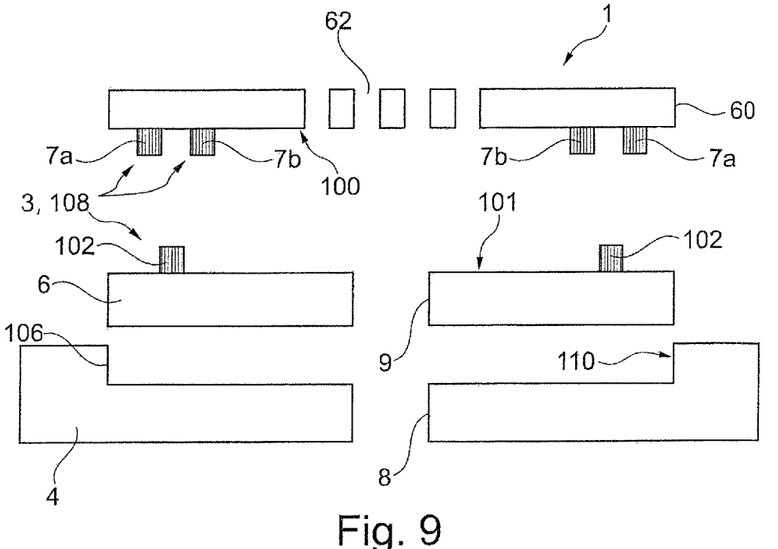

The embodiment shown in FIG. 9 differs from the embodiment shown in FIGS. 3 and 8 in that a plurality of sealing members 7a, 7b are arranged between the heating body 60 and the seal carrier 6, in this case two. The sealing device 3 comprises two sealing members 7a, 7b and the seal carrier 6 having the seal member 102. The sealing device 3 forms a labyrinth seal 108 in the assembled state. This embodiment is particularly liquid-sealed and thermally decouples the heating body 60 and the carrier in a particularly effective manner.

In FIG. 9 the sealing members 7a, 7b are arranged concentrically around the passage openings 62. Therefore, the sealing members 7a, 7b enclose the passage openings 62 completely and in a liquid-sealed manner. The sealing members 7a, 7b are radially spaced from one another beginning at the passage openings 62. In other embodiments, for example, one of the sealing members 7a, 7b can only partially enclose the passage openings 62, especially in particularly exposed regions where leakage is most probable. Additionally, one of the sealing members 7a, 7b can, for example, be formed as a labyrinth in the edge region of the passage opening 62, in order to achieve an additional fluidic sealing effect against an unintentionally leaking fluid, e.g. due to pressure fluctuations, such as short-term overpressure.

In the embodiment according to FIGS. 8 and 9, a plurality of seal members 102a, 102b (not shown in the drawings) can also be arranged on the seal carrier 6. The labyrinth seal 108 described above and/or the inserting of a sealing member 7 into a recess 105 can be used as a positioning or assembly aid and/or additional mechanical fixing of the heating body 60 to the carrier 4.

Figure 10:
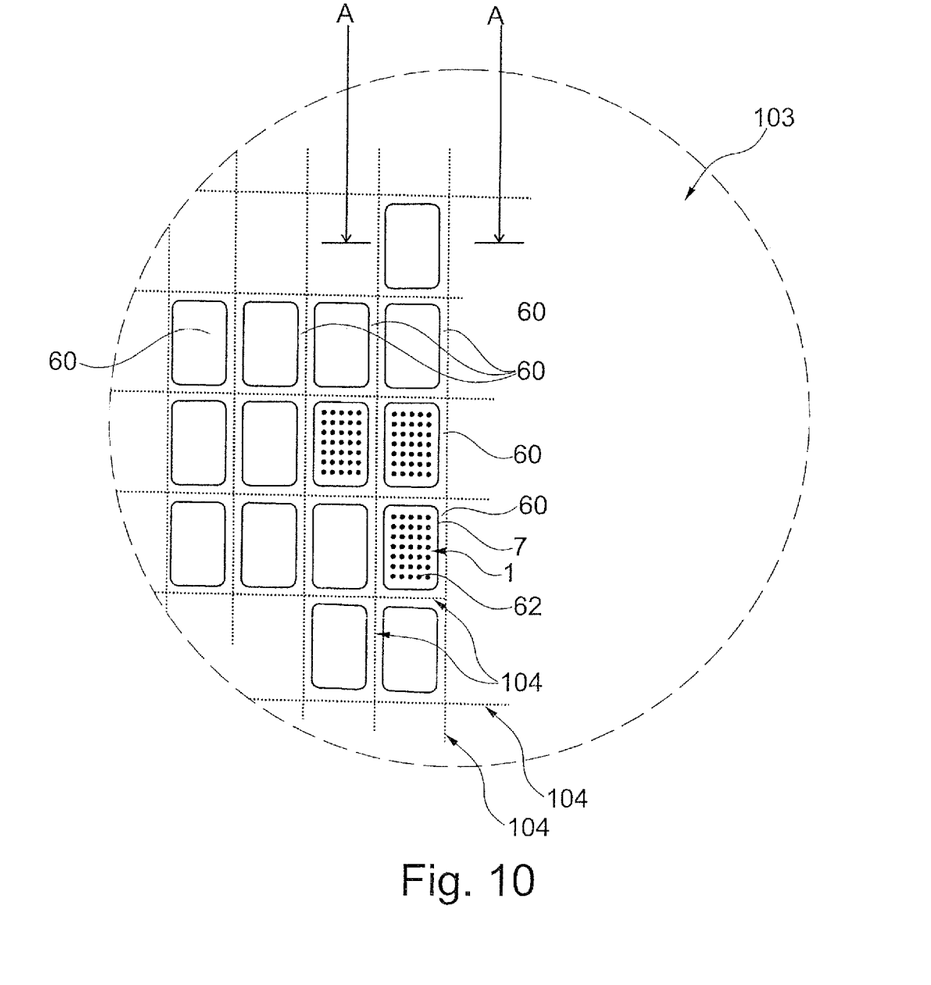
FIGS. 10 and 11 are a schematic top view and a cross-sectional view of a plurality of heating bodies.
Figure 11:
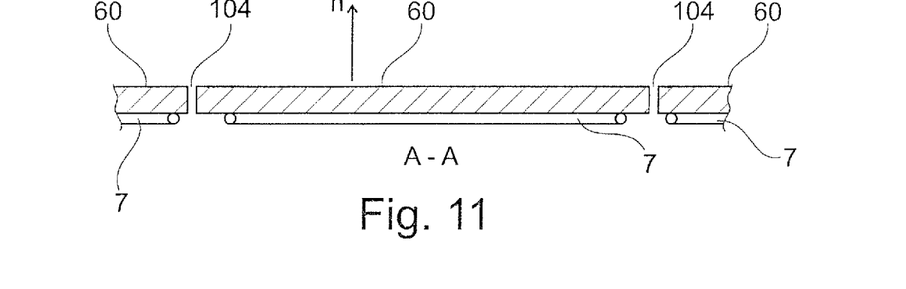

FIG. 10 shows a plurality of heating bodies 60 in a schematic plan view and FIG. 11 shows the plurality of heating bodies 60 in a cross-sectional representation in a plane through which the line A shown in FIG. 10 runs.

The heating bodies 60 are available as semiconductor chips, each of which has a field in its middle region having a plurality of passage openings 62 with which the heating bodies 60 are perforated so as to be permeable to liquid. The passage openings 62 in FIG. 10 are only indicated as points for some heating bodies 60, but are explained in more detail with reference to FIG. 13.

FIGS. 10 and 11 illustrate the method according to the invention for manufacturing a plurality of electrically heatable heating bodies 60 having at least one passage opening 62 for evaporating liquid contained in the passage opening 62.

A plate-like semiconductor material 103 is provided. The semiconductor material 103 is advantageously metal-free, for example made of silicon, in order to avoid a harmful release of metal component parts and/or metal atoms or ions or a harmful catalytic effect of metal component parts during the evaporation through the heating body 60.

The plate-like semiconductor material 103 is substantially flat and has a well-defined normal surface n indicated in FIG. 11 which is perpendicular to the plate-like semiconductor material 103. The plate-like semiconductor material 103 is in the form of a wafer having a diameter of, for example, 8 inches and has two opposite sides, which can be described as the top and bottom sides.

At least one insulating layer can be applied to at least one of the two sides, for example of silicon nitride and/or silicon oxynitride. Another or further insulating layer may be formed of thermal oxide. For example, the insulation can be applied by gas deposition.

Polysilicon can be applied onto the semiconductor material 103, for example also by gas deposition, in order to provide the heating bodies 60 to be manufactured with a heat-conducting layer (NTC layer).

A plurality of passage openings 62 extending in the direction normal to the surface through the semiconductor material 103 are incorporated into the semiconductor material 103, for example by photolithography.

The semiconductor material 103 is separated along one or a plurality of separation lines 104 to provide the plurality of heating bodies 60. This step called "dicing" separates the semiconductor material 103 into individual heating bodies 60 or groups of heating bodies 60. Between 1000 and 10000, preferably between 2000 and 6000, for example about 4200 heating bodies 60 can be cut out of the semiconductor material 103, in the form of an 8-inch wafer.

According to the invention, a number of sealing members 7 corresponding to at least the number of heating bodies 60 is arranged in such a manner that each passage opening 62 is surrounded circumferentially by a sealing member 7. Therefore, a later leakage in the direction of the liquid supply of an evaporator device 1 can be avoided comprehensively using the heating body 60 during the manufacturing of a heating body 60. For this purpose, sealing webs or sealing members 7 are applied around the contours of the respective passage openings 62.

Each heating body 60, for example, is coated with an advantageously thermally stable plastic. For example, each heating body 60 has a sealing member 7 after the manufacture.

This means that a sealing device 3 described with reference to FIGS. 1 to 9 has a sealing member 7, wherein the sealing member 7 surrounds the passage opening 62 in a sealing manner in the assembled state and the sealing device 3 is arranged between the heating body 60 and a carrier 4 of an evaporator device 1 in the correct assembly.

Before the semiconductor material 103 is separated, the sealing members 7 are advantageously arranged or applied around the passage openings 62 of the respective heating bodies 60 in order to manufacture heating bodies 60 as effectively as possible. The sealing members 7 are applied to the semiconductor material 103 like a template. In other embodiments, the sealing members 7 can also be applied after cutting the semiconductor material 103 in order to avoid endangering the quality of the sealing members 7 by cutting them.

The sealing members 7 are advantageously made of temperature-resistant silicone and/or rubber. The material of the sealing member 7 is advantageously chosen in such a manner that it is temperature-resistant and sufficiently inert after the manufacture. The applied sealing web or the applied sealing member 7 can be adjusted to the requirements of the liquid sealing and thermal decoupling between the heating bodies 60 and a carrier 4 by varying the geometry, i.e. thickness, width, shape, imprint pattern.

It is advantageous for the arrangement or geometric design of the sealing members 7 to optimally design both the heating member 60 and the sealing member 7, e.g. by providing functional regions on the heating bodies 60 which are recessed by the sealing member 7.

It is advantageous to arrange the sealing members 7 in a liquid state, for example by injecting, injection moulding, spraying, 3D printing, casting and/or the application of a welding bead. The arranging of the sealing members 7 can also be applied to the wafer or the semiconductor material 103 by means of printing methods such as pad printing or screen printing methods, for example.

The sealing members 7 are advantageously connected in a material-tight manner to the semiconductor material 103 and/or the heating body 60 during the arranging.

After applying, the sealing member 7 hardens advantageously, wherein the sealing member 7 is advantageously softer than the semiconductor material 103 after hardening, i.e. the sealing member 7 assumes a defined elasticity during hardening after the application, said elasticity being softer than that of the semiconductor material 103.

Figure 12:
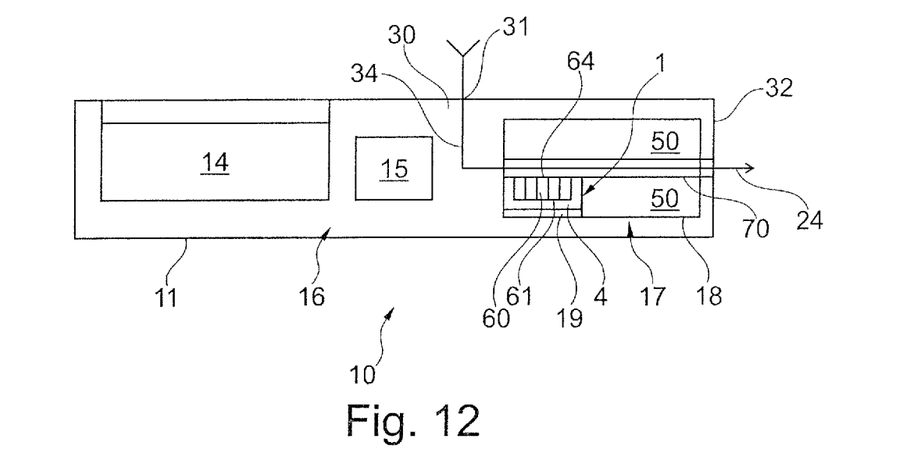
FIG. 12 is a schematic representation of an inhaler.

FIG. 12 schematically shows an inhaler 10. The inhaler 10, in this case an electronic cigarette product, comprises a housing 11 in which an air channel 30 is provided between at least one air inlet opening 31 and one air outlet opening 24 at a mouth end 32 of the cigarette product 10. The mouth end 32 of the cigarette product 10 is the end at which the consumer inhales by applying a negative pressure to the cigarette product 10 and generating an air stream 34 in the air channel 30.

The cigarette product 10 consists advantageously of a base part 16 and a consumable unit 17, which comprises the evaporator device 1 and the liquid store 18 and is formed in particular in the form of an exchangeable cartridge. The air sucked in through the inlet opening 31 is directed in the air channel 30 to or through at least one evaporator device 1. The evaporator device 1 is connected or can be connected to the liquid store 18 in which at least one liquid 50 is stored.

The evaporator device 1 evaporates liquid 50, which is advantageously supplied to the evaporator device 1 from the liquid store 18 from a wick or a wick structure 19 by means of capillary forces, and adds the evaporated liquid as aerosol/vapour at an outlet side 64 into the air stream 34.

The porous and/or capillary, liquid-conducting wick structure 19 is advantageously arranged on an inlet side 61 of the heating body 60, as shown schematically in FIG. 12. The link shown in FIG. 12 between the wick structure 19 and the liquid store 18 and the heating body 60 via the carrier 4 is only exemplary. In particular, a fluid interface and/or a plurality of fluid conduits can be provided between the fluid store 18 and the wick structure 19. The liquid store 18 can therefore also be arranged at a distance from the wick structure 19. The wick structure 19 contacts the inlet side 61 of the heating body 60 advantageously in a flat manner and covers all passage openings 62 on the inlet side. On the side opposite the heating body 60, the wick structure is connected to the liquid store 18 in a fluid-conducting manner. The dimensions of the liquid store 18 can be larger than those of the wick structure 19. The wick structure 19 can, for example, be inserted into an opening in a housing of the liquid store 18. A plurality of evaporator devices 1 can be associated with a liquid store 18. The wick structure 19 can generally consist of one or a plurality of parts.

The wick structure 19 consists of porous and/or capillary material which, due to capillary forces, is able to passively convey sufficient liquid evaporated from the heating body 60 from the liquid store 18 to the heating body 60 in order to prevent the passage openings 62 from running empty and to prevent problems resulting therefrom.

The wick structure 19 consists advantageously of an electrically non-conductive material in order to avoid an undesired heating of the liquid in the wick structure 19 by current flow. The wick structure 19 has advantageously a low thermal conductivity. The wick structure 19 consists advantageously of one or a plurality of the following materials: cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable conveying rate, or a combination of two or a plurality of the materials mentioned above. In an advantageous practical embodiment, the wick structure 19 may comprise at least one ceramic fibre paper and/or one porous ceramic. The volume of the wick structure 19 is preferably in the range between 1 mm$^3$ and 10 mm$^3$, further preferably in the range between 2 mm$^3$ and 8 mm$^3$, even further preferably in the range between 3 mm$^3$ and 7 mm$^3$ and is, for example, 5 mm$^3$.

An insulating layer of an electrically and/or thermally insulating material, for example glass, ceramic or plastic, having openings extending through the insulating layer and corresponding to the passage openings 62, is advantageously provided between the wick structure 19 and the heating body 60, if the wick structure 19 in consists of an electrically and/or thermally conductive material, which is not excluded.

An advantageous volume of the liquid store 18 lies in the range between 0.1 ml and 5 ml, preferably between 0.5 ml and 3 ml, further preferably between 0.7 ml and 2 ml or 1.5 ml.

The electronic cigarette 10 also comprises an electrical energy store 14 and an electronic control device 15. The energy store 14 is usually arranged in the base part 16 and can be, in particular, a disposable electrochemical battery or a rechargeable electrochemical battery, for example a lithium-ion battery. The consumable unit 17 is arranged between the energy store 14 and the mouth end 32. The electronic control device 15 comprises at least one digital data processing apparatus, in particular a microprocessor and/or microcontroller, in the base part 16 (as shown in FIG. 12) and/or in the consumable unit 17.

A sensor, such as a pressure sensor or a pressure or flow switch, is advantageously arranged in the housing 11, wherein the control device 15 can determine, on the basis of a sensor signal output from the sensor, that a consumer is puffing 32 the cigarette product 10 at the mouth end to inhale. In this case, the control device 15 controls the evaporator device 1 to add liquid 50 from the liquid store 18 as aerosol/vapour into the air stream 34.

The evaporator device 1 or at least one evaporator 60 is arranged in a part of the consumable unit 17 facing away from the mouth end 32. This enables effective electrical coupling and an activation of the evaporator device 1. The air stream 34 leads advantageously through an air channel 70 running axially through the liquid store 18 to the air outlet opening 24.

The liquid 50 stored in the liquid store 18 to be dosed is, for example, a mixture of 1,2-propylene glycol, glycerine, water, at least one flavour and/or at least one active substance, in particular nicotine.

However, the specified component parts of the liquid 50 are not mandatory. In particular, aroma and/or active substances, in particular nicotine, can be avoided.

The consumable unit or cartridge 17 or the base part 16 advantageously comprises a non-volatile data storage device for storing information or parameters relating to the consumable unit or cartridge 17. The data storage may be part of the electronic control device 15. The data storage is advantageously used to store information regarding the composition of the liquid stored in the liquid store 18, information regarding the process profile, in particular power/temperature control; data for condition monitoring or system testing, for example seal testing; data regarding copy protection and counterfeit protection, an ID for unique identification of the consumable unit or cartridge 17, serial number, date of manufacture and/or expiry date, and/or number of puffs (number of inhalation puffs by the consumer) or the period of use. The data storage is advantageously electrically connected or can be connected to the control unit 15.

User-related data, in particular on smoking behaviour, could also be stored in the inhaler 10 and/or in an external storage, which can be connected to the inhaler 10 in a suitable and known manner, at least temporarily, in terms of communication technology, and could preferably also be used to control and regulate the inhaler.

Figure 13:
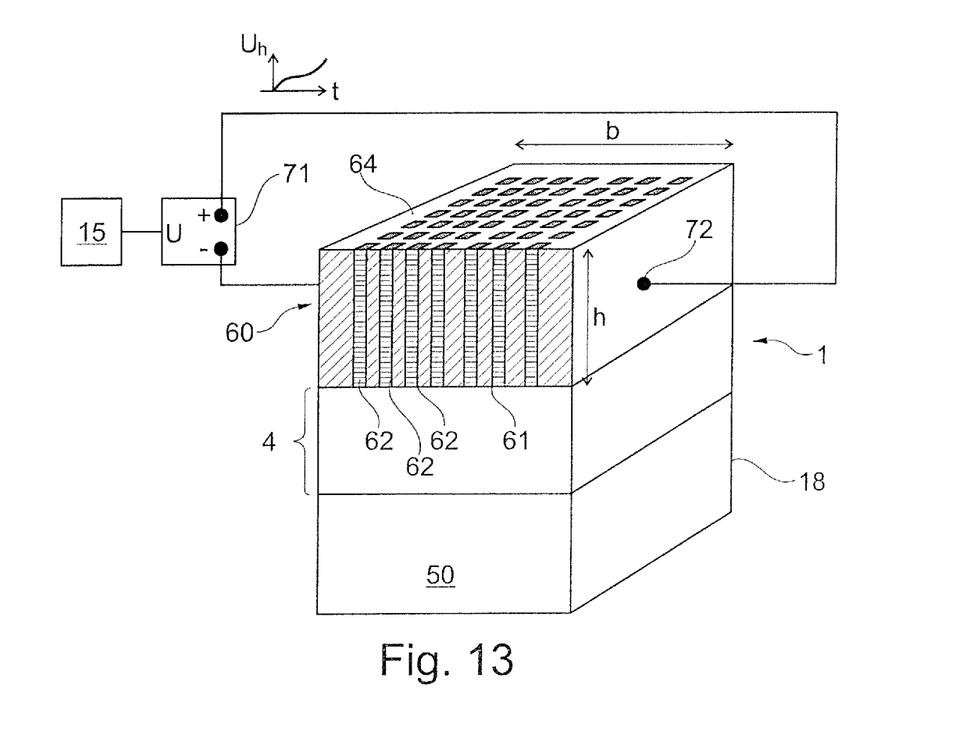
FIG. 13 is a perspective cross-sectional view of a heating body having a liquid store.

FIG. 13 shows an evaporator device 1. The evaporator device 1 comprises a block-like, preferably monolithic heating body 60, preferably made of an electrically conductive material, in particular a semiconductor material, preferably silicon, and a carrier 4. It is not necessary for the entire heating body 60 to be made of an electrically conductive material. It may be sufficient, for example, that the surface of the heating body 60 is electrically conductive, e.g. metallic, coated or preferably suitably doped. In this case, the entire surface does not have to be coated, for example metallic or preferably non-metallic or non-metallic laminated metallic conductor webs can be provided on a non-conductive or semi-conductive base body. It is also not absolutely necessary for the entire heating body 60 to heat; it may be sufficient, for example, if a portion or a heating layer of the heating body 60 heats in the region of the outlet side 64.

The heating body 60 is provided with a plurality of micro-channels or passage openings 62, which connect an inlet side 61 of the heating body 60 with an outlet side 64 of the heating body 60 in a liquid-conducting manner. The inlet side 61 is connected to the liquid store 18 via a wick structure 19 in liquid-conducting manner not shown in FIG. 13. The wick structure 19 is used for the passive conveyance of liquid from the liquid store 18 to the heating body 60 by means of capillary forces.

The median diameter of the passage openings 62 is preferably in the range between 5 μm and 200 μm, further preferably in the range between 30 μm and 150 μm, even further preferably in the range between 50 μm and 100 μm. Due to these dimensions, a capillary effect is advantageously generated, so that liquid penetrating into a passage opening 62 at the inlet side 61 rises upwards through the passage opening 62 until the passage opening 62 is filled with liquid. The volume ratio of the passage openings 62 to the heating body 60, which can be referred to as the porosity of the heating body 60, is for example in the range between 10% and 50%, advantageously in the range between 15% and 40%, further advantageously in the range between 20% and 30%, and is, for example, 25%.

The edge lengths of the surfaces of the heating body 60 provided with passage openings 62, for example, are in the range between 0.5 mm and 3 mm, preferably between 0.5 mm and 1 mm. For example, the dimensions of the surfaces of the heating body 60 provided with passage openings 62 can be as follows: 0.95 mm×1.75 mm or 1.9 mm×1.75 mm or 1.9 mm×0.75 mm. The edge lengths of the heating body 60 can be, for example, in the range between 0.5 mm and 5 mm, preferably in the range between 0.75 mm and 4 mm, further preferably in the range between 1 mm and 3 mm. The surface of the heating body 60 (chip size), for example, can be 1 mm×3 mm, 2 mm×2 mm or 2 mm×3 mm.

The width b of the heating body 60 (see FIG. 13) is preferably in the range between 1 mm and 5 mm, further preferably in the range between 2 mm and 4 mm, and is, for example, 3 mm. The height h of the heating body 60 (see FIG. 13) is preferably in the range between 0.05 mm and 1 mm, further preferably in the range between 0.1 mm and 0.75 mm, even further preferably in the range between 0.2 mm and 0.5 mm, and is, for example, 0.3 mm. Even smaller heating bodies 60 can be manufactured, designed and operated in a functional manner.

The number of passage openings 62 is preferably in the range between four and 1000. This allows the heat input into the passage openings 62 to be optimised and ensures a high evaporation capacity and a sufficiently large steam outlet surface.

The passage openings 62 are arranged in the form of a square, rectangular, polygonal, round, oval or differently shaped array. The array may be in the form of a matrix having s columns and z rows, wherein s is advantageously in the range between 2 and 50 and further advantageously in the range between 3 and 30 and/or z is advantageously in the range between 2 and 50 and further advantageously in the range between 3 and 30. This allows for an effective and easily manufactured arrangement of passage openings 62 having a secured high evaporation capacity.

The cross-section of the passage openings 62 can be square, rectangular, polygonal, round, oval or otherwise shaped and/or vary lengthwise in portions, in particular may increase, decrease or remain constant.

The length of one or each passage opening 62 is preferably in the range between 100 μm and 1000 μm, further preferably in the range between 150 μm and 750 μm, even further preferably in the range between 180 μm and 500 μm, and is, for example, 300 μm. This allows an optimum liquid absorption and a portion formation with sufficient heat input from the heating body 60 into the passage openings 62.

The distance between two passage openings 62 is preferably at least 1.3 times the clear diameter of one passage opening 62, wherein the distance refers to the centre axes of the two passage openings 62. The distance can preferably be 1.5 to 5 times the clear diameter of a passage opening 62, further preferably 2 to 4 times. This allows an optimum heat input into the heating body 60 and a sufficiently stable arrangement and wall thickness of the passage openings 62.

Due to the features described above, the heating body 60 can also be described as a volume heater.

The evaporator device 1 has a heating voltage source 71, preferably controllable by the control device 29, which is connected via electrodes 72 to opposite sides of the heating body 60, in such a manner that an electrical voltage Uh generated by the heating voltage source 71 leads to a current flow through the heating body 60. Due to the ohmic resistance of the electrically conductive heating body 60, the current flow leads to heating of the heating body 60 and therefore to evaporation of the liquid contained in the passage openings 62. The vapour/aerosol 6 generated in this manner escapes to the outlet side 64 from the passage openings 62 and is added to the air stream 34, see FIG. 12. More precisely, upon detection of an air stream 34 caused by the consumer puffing through the air channel 30, the control device 29 controls the heating voltage source 71, wherein the liquid in the passage openings 62 in the form of vapour/aerosol 6 is driven out of the passage openings 62 by spontaneous heating.

The duration of the individual evaporation steps at different temperatures and/or an evaporation of the individual components of the individual portions of the liquid can be kept so short and/or clocked using an activation frequency that the step-by-step evaporation cannot be perceived by a consumer and nevertheless a largely homogeneous, taste conform, repeatable precise aerosol formation can be guaranteed. In particular, it is advantageous to first evaporate a low-boiling component of the liquid in a first evaporation interval at a first temperature A, and then to evaporate a high-boiling component of the liquid in a second evaporation interval at a second temperature B, which exceeds the temperature A.

An electronic or electrical link to the heating body 60 can, for example, be made via clamping, spring or press contacts, wire bonding and/or soldering.

A voltage curve Uh(t) adjusted to the liquid mixture used is preferably stored in the data storage of the inhaler 10. This makes it possible to set the voltage curve Uh(t) according to the liquid used, so that the heating temperature of the heating body 60, and therefore also the temperature of the capillary passage openings 62, can be controlled in accordance with the known evaporation kinetics of the respective liquid over time during the evaporation procedure, thus achieving optimum evaporation results. The evaporation temperature is preferably in the range between 100° C. and 400° C., further preferably between 150° C. and 350° C., even further preferably between 190° C. and 290° C.

The heating body 60 can be advantageously manufactured from parts of a wafer using thin film layer technology, which has a layer thickness of preferably less than or equal to 1000 μm, further preferably 750 μm, even further preferably less than or equal to 500 μm. The surfaces of the heating body 60 can advantageously be hydrophilic. The outlet side 64 of the heating body 60 can advantageously be microstructured or have micro grooves.

The evaporator device 1 is set in such a manner that a quantity of liquid is added preferably in the range between 1 μl and 20 μl, further preferably between 2 μl and 10 μl, even further preferably between 3 μl and 5 μl, typically 4 μl per puff of the consumer. The evaporator device 1 can preferably be adjusted with regard to the liquid/vapour quantity per puff, i.e. from 1 s to 3 s per puff duration.

In the following, the course of the evaporation procedure is explained as an example.

In an initial state, the voltage source 71 or the energy storage 14 is switched off for the heating procedure.

To evaporate liquid 50, the voltage source 14, 71 for the heating body 60 is activated. The voltage Uh is set in such a manner that the evaporation temperature in the heating body 60 and therefore in the passage openings 62 is adapted to the individual evaporation behaviour of the liquid mixture used. This prevents the danger of local overheating and thereby the formation of harmful substances.

In particular, an undesired differential evaporation of a liquid mixture can be counteracted or avoided or prevented. A liquid mixture could otherwise lose components prematurely due to different boiling temperatures in the course of a sequence of evaporation procedures, in particular "puffs", before the reservoir 18 of the liquid 50 is completely emptied, which could result in undesirable effects during operation, such as the lack of consistency of dosage for a user, in particular for a pharmaceutically active liquid.

As soon as a quantity of liquid equal to or related to the volume of the passage openings 62 has evaporated, the heating voltage source 71 is deactivated. Since the liquid properties and quantity are advantageously known exactly and the heating body 60 has a measurable temperature-dependent resistance, this moment can be very precisely determined or controlled. The energy consumption of the evaporator device 1 can therefore be reduced compared to known devices, since the required evaporation energy can be dosed and thereby introduced more precisely.

After the completion of the heating procedure, the passage openings 62 are predominantly or completely emptied. The heating voltage 71 is then kept switched off until the passage openings 62 are replenished by feeding liquid through the wick structure 19. When this happens, the next heating cycle can be started by switching on the heating voltage 71.

The activation frequency of the heating body 60 generated by the heating voltage source 71 is generally advantageous in the range from 1 Hz to 50 kHz, preferably in the range from 30 Hz to 30 kHz, and even further advantageous in the range from 100 Hz to 25 kHz.

The frequency and the duty factor of the heating voltage Uh for the heating body 60 are advantageously adjusted to the natural oscillation or natural frequency of the bubble oscillations during bubble boiling. The period duration 1/f of the heating voltage can be advantageously in the range between 5 ms and 50 ms, further advantageously between 10 ms and 40 ms, even further advantageously between 15 ms and 30 ms and, for example, 20 ms. Depending on the composition of the evaporated liquid 50, frequencies other than those specified can be optimally adjusted to the natural oscillation or natural frequency of the bubble oscillations.

Furthermore, it has been found that the maximum heating current generated by the heating voltage Uh should preferably not exceed 7 A, further preferably not exceed 6.5 A, even further preferably not exceed 6 A and should ideally be in the range between 4 A and 6 A in order to ensure concentrated vapour while avoiding overheating.

The delivery rate of the wick structure 19 is in turn optimally adjusted to the evaporation rate of the heating body 60, so that sufficient liquid can be delivered at any time and draining of the region in front of the heating body 60 is avoided.

The evaporator device 1 is preferably produced on the basis of MEMS technology, in particular silicon, and is therefore advantageously a micro-electro-mechanical system.

According to the above, a layered construction consisting of a Si-based heating body 60, which at least on the inlet side 61 is advantageously planar, and of one or a plurality of capillary structures 19 lying underneath having advantageously different pore sizes is proposed. The wick structure 19 arranged directly on the inlet side 61 of the heating body 60 prevents the formation of bubbles on the inlet side 61 of the heating body 60, as gas bubbles prevent a further conveying effect and at the same time lead to a (local) overheating of the heating body 60 due to a lack of cooling by liquid flowing in.

EMBODIMENTS

Embodiment 1

Evaporator device (1) for an inhaler (10), in particular for an electronic cigarette product, comprising:
an electrically heatable heating body (60) having at least one passage opening (62) for evaporating liquid contained in the passage opening (62), and
a carrier (4) for retaining the heating body (60), characterised in that the evaporator device (1) has a sealing device (3), and
the sealing device (3) is arranged between the heating body (60) and the carrier (4) and encloses the at least one passage opening (62) in a sealing manner.

Embodiment 2

Evaporator device (1) according to embodiment 1, characterised in that
the sealing device (3) completely encloses the at least one passage opening (62).

Embodiment 3

Evaporator device (1) according to any of the preceding embodiments, characterised in that:
a surface (101) contacting the sealing device (3) has a recess (105) corresponding to the geometry of the sealing device (3) for inserting the sealing device (3).

Embodiment 4

Evaporator device (1) according to any of the preceding embodiments, characterised in that
the sealing device (3) and the heating body (60) are interconnected in a material-tight manner.

Embodiment 5

Evaporator device (1) according to any of the preceding embodiments, characterised in that
the sealing device (3) comprises one or a plurality of sealing members (7, 7a, 7b).

Embodiment 6

Evaporator device (1) according to any of the preceding embodiments, characterised in that
the sealing device (3) is softer, in particular has a lower modulus of elasticity than the heating body (60) and/or the carrier (4).

Embodiment 7

Evaporator device (1) according to any of the preceding embodiments, characterised in that
the evaporator device (1) comprises a substrate (5) arranged between the carrier (4) and the heating body (60) for the thermal decoupling of the heating body (60) and the carrier (4).

Embodiment 8

Evaporator device (1) according to any of the preceding embodiments, characterised in that the evaporator device (1) has a seal carrier (6) arranged between the carrier (4) and the heating body (60), wherein
the seal carrier (6) comprises at least one seal member (102, 102a, 102b).

Embodiment 9

Evaporator device (1) according to any of the preceding embodiments, characterised in that
the sealing device (3) forms a labyrinth seal (108).

Embodiment 10

Consumable unit (17) comprising an evaporator device (1) according to any of the preceding embodiments.

Embodiment 11

Inhaler (10) comprising an evaporator device (1) according to any of the preceding embodiments 1 to 9.

Embodiment 12

Method for manufacturing a plurality of electrically heatable heating bodies (60) for an evaporator device and having at least one passage opening (62) for evaporating liquid contained in the passage opening (62), comprising
providing a plate-like semiconductor material (103),
incorporating a plurality of passage openings (62) extending in the direction normal to the surface of the semiconductor material (103) through the semiconductor material (103),
separating the semiconductor material (103) along at least one separation line (104) to provide the plurality of heating bodies (60), characterised by
arranging a number of sealing members (7, 7a, 7b) corresponding to at least the number of heating bodies (60) in such a manner that each passage opening (62) is circumferentially enclosed by a sealing member (7, 7a, 7b).

Embodiment 13

Method according to embodiment 12, characterised in that
the sealing members (7, 7a, 7b) are arranged before the semiconductor material (103) is separated.

Embodiment 14

Method according to embodiment 12 or 13, characterized by
arranging the sealing members (7, 7a, 7b) in a liquid state.

Embodiment 15

Method according to any of the preceding embodiments 12 to 14, characterised in that
the sealing members (7, 7a, 7b) are connected in a material-tight manner to the semiconductor material (103) and/or the heating body (60) during the arranging.

Embodiment 16

Method for manufacturing a plurality of seal carriers (6) for sealing electrically heatable heating bodies (60) for an evaporator device and having at least one liquid opening (9) for conducting liquid, comprising
providing a plate-like material,
incorporating a plurality of liquid openings (9) extending through the material in the direction normal to the surface of the material,
separating the material along at least one separation line to provide the plurality of seal carriers (6), and
arranging a number of seal members (102, 102a, 102b) corresponding to at least the number of seal carriers (6) in such a manner that each liquid opening (9) is circumferentially enclosed by a seal member (102, 102a, 102b).

The invention claimed is:

1. An evaporator device for an inhaler, for an electronic cigarette product, comprising:
a heating body having at least one passage opening for evaporating liquid contained in the passage opening, wherein the heating body is electrically heated:
a carrier for retaining the heating body; and
a sealing device,
wherein the sealing device is arranged between the heating body and the carrier and encloses the at least one passage opening in a sealing manner,
wherein a surface of the carrier contacting the sealing device has a recess corresponding to the geometry of the sealing device for inserting the sealing device.

2. The evaporator device according to claim 1,
wherein the sealing device completely encloses the at least one passage opening.

3. A method for manufacturing a plurality of seal carriers for sealing electrically heatable heating bodies for an evaporator device, each seal carrier having at least one liquid opening for conducting liquid, comprising:
providing a plate-like material;
incorporating a plurality of liquid openings extending through the plate-like material in the direction normal to a surface of the plate-like material;
separating the plate-like material along at least one separation line to provide a plurality of seal carriers each seal carrier having at least one liquid opening for conducting liquid; and
arranging a number of seal members corresponding to at least the number of seal carriers in such a manner that each liquid opening of the at least one liquid opening is circumferentially enclosed by a seal member of the number of sealing members.

4. The evaporator device according to claim 1,
wherein the sealing device and the heating body are interconnected in a material-tight manner.

5. The evaporator device according to claim 1,
wherein the sealing device comprises one or more sealing members.

6. The evaporator device according to claim 1,
wherein the sealing device has a lower modulus of elasticity than the heating body and/or the carrier.

7. The evaporator device according to claim 1, further comprising:
a substrate arranged between the carrier and the heating body for the thermal decoupling of the heating body and the carrier.

8. The evaporator device according to claim 1, further comprising:
a seal carrier arranged between the carrier and the heating body,
wherein the seal carrier comprises at least one seal member.

9. The evaporator device according to claim 1, wherein the sealing device forms a labyrinth seal.

10. A consumable unit comprising an evaporator device according to claim 1.

11. An inhaler comprising an evaporator device according to claim 1.

12. A method for manufacturing a plurality of electrically heatable heating bodies for an evaporator device, each electrically heatable heating body having at least one passage opening for evaporating liquid contained in the at least one passage opening, comprising:
    providing a semiconductor material,
    wherein the semiconductor material is plate-like;
    incorporating a plurality of passage openings extending in the direction normal to the surface of the semiconductor material through the semiconductor material;
    separating the semiconductor material along at least one separation line to provide the plurality of electrically heatable heating bodies, each having at least one passage opening of the plurality of passage openings; and
    arranging a number of sealing members corresponding to at least the number of electrically heatable heating bodies in such a manner that each passage opening of the at least one passage opening is circumferentially enclosed by a sealing member of the number of sealing members.

13. The method according to claim 12, wherein the number of sealing members are arranged before the semiconductor material is separated.

14. The method according to claim 12, wherein arranging the number of sealing members comprises arranging the number of sealing members in a liquid state.

15. The method according to claim 12, wherein the number of sealing members are connected in a material-tight manner to the semiconductor material and/or the electrically heatable heating body during arranging the number of sealing members.

* * * * *